US00PP27980P3

(12) United States Plant Patent
Castellarin et al.

(10) Patent No.: US PP27,980 P3
(45) Date of Patent: May 9, 2017

(54) GRAPEVINE NAMED 'SAUVIGNON KRETOS'

(50) Latin Name: ***Vitis×vinifera* (hybrid)**
Varietal Denomination: SAUVIGNON KRETOS

(71) Applicants: Università degli Studi di Udine, Udine UD (IT); Istituto di Genomica Applicata, Udine UD (IT)

(72) Inventors: Simone Diego Castellarin, Vancouver (CA); Guido Cipriani, Faedis (IT); Gabriele Di Gaspero, Cividale del Friuli UD (IT); Michele Morgante, Tricesimo UD (IT); Enrico Peterlunger, Codroipo UD (IT); Raffaele Testolin, Udine (IT)

(73) Assignees: Università degli Studi di Udine, Udine (IT); Istituto di Genomica Applicata, Udine (IT)

( * ) Notice: Subject to any disclaimer, the term of this patent is extended or adjusted under 35 U.S.C. 154(b) by 0 days.

(21) Appl. No.: 14/545,098

(22) Filed: Mar. 26, 2015

(65) Prior Publication Data

US 2016/0242338 P1 Aug. 18, 2016

(30) Foreign Application Priority Data

Feb. 13, 2015 (QZ) ..... PBR 2015/0368

(51) Int. Cl.
*A01H 5/08* (2006.01)

(52) U.S. Cl.
USPC ..... Plt./207

(58) Field of Classification Search
USPC ..... Plt./207
See application file for complete search history.

*Primary Examiner* — Annette Para
(74) *Attorney, Agent, or Firm* — Foley & Lardner LLP

(57) ABSTRACT

A new and distinct variety of grapevine named 'SAUVIGNON KRETOS', primarily adapted to the growing conditions of the temperate regions, and characterized by its strong vigor; erect growth habit; wedge-shaped leaves with medium texture; medium weight and conical shaped berry clusters; early maturing, firm berry flesh with no coloration and neutral taste primarily for winemaking; early harvesting time; and resistance to winter temperatures (to −22° C.), resistance to downy mildew and tolerance to powdery mildew.

4 Drawing Sheets

Latin name of the genus and species of the plant claimed: *Vitis×vinifera* (hybrid).

Variety name: 'SAUVIGNON KRETOS'.

BACKGROUND OF THE INVENTION

The present invention relates to a new and distinct summer/fall bearing grapevine variety, botanically known as *Vitis vinifera*, and hereinafter referred to by the name 'SAUVIGNON KRETOS'.

The new grapevine 'SAUVIGNON KRETOS' is a product of a controlled breeding program conducted by the inventors in Udine, Italy. The objective of the breeding program was to develop a new grapevine variety particularly characterized by resistance to cold (<−20° C.), resistance to downy mildew (*Plasmopara viticola*), and tolerance to powdery mildew (*Uncinula necator*).

The new grapevine 'SAUVIGNON KRETOS' originated from a cross made by the inventors in 2002 in Udine, Italy. The female or seed parent is the grapevine variety *Vitis vinifera* 'Sauvignon' (unpatented), and the male or pollen parent is the grapevine variety *Vitis* '20/3' (Bianca×SK77-4/5) (unpatented).

The new grapevine 'SAUVIGNON KRETOS' was discovered and selected by the inventors as a single flowering plant within the progeny of the stated cross in a controlled environment in 2002 in Udine, Italy. Asexual reproduction of the new grapevine variety by grafting was first performed in February 2004 in Rauscedo, Friuli Venezia Giulia region, Italy, and has demonstrated that the combination of characteristics as herein disclosed for the new cultivar are firmly fixed and retained through successive generations of asexual reproduction. The new cultivar reproduces true to type.

SUMMARY OF THE INVENTION

'SAUVIGNON KRETOS' is primarily adapted to the climate and growing conditions of the temperate regions with average yearly temperature about 13° C., minimum winter temperature about −20° C., annual rainfall around 700-1500 mm of rain (e.g. North-Eastern Italy, Friuli). This region provides the necessary year-round temperatures required for it to produce and maintain a strong vigorous plant with consistent fruit production from April through November on primocanes and in the ensuing year from April through November on the floricanes.

The following traits have been repeatedly observed and are determined to be unique characteristics of 'SAUVIGNON KRETOS', which in combination distinguish this grapevine plant as a new and distinct variety.

1. Strong vigor;
2. Erect growth habit;
3. Wedge-shaped leaves with a medium green upper surface and light green lower surface and a medium texture;
4. Fruit clusters with medium weight, conical shape, firm berry flesh with neutral taste, and no flesh coloration, early maturity (end of August in Middle Friuli, North-Eastern Italy); and primarily used for wine.

5. Primocanes and floricanes with an elliptic cross section, brownish color, no lenticels, and small internodes of 8 mm diameter;
6. Early harvesting time, at end of August in Middle Friuli, North-Eastern Italy; and
7. Resistance to winter temperature (−22° C.), resistance to downy mildew, and tolerant to powdery mildew, if overripening is allowed it is susceptible to cluster rots.

Plants of the new grapevine 'SAUVIGNON KRETOS' differ from plants of the parents, *Vitis vinifera* 'Sauvignon' (unpatented) and *Vitis* '20/3' (unpatented), in the following characteristics described in Table 1.

TABLE 1

Comparison with Parent Varieties

| Characteristic | New Cultivar 'SAUVIGNON KRETOS' | Female Parent 'Sauvignon' ( unpatented) | Male Parent '20/3' ( unpatented) |
|---|---|---|---|
| vigor | strong | medium | medium |
| growth habit | erect | semi-erect | semi-erect |
| leaf | medium, medium green color (upper surface), light green color (lower surface), no hairs in both surfaces, wedge-shaped, medium texture, | medium, medium green color (upper surface), pale green color (lower surface), prostrate hairs on upper surface: present, high density of prostrate hairs on lower surface, circular shape, medium texture | Medium size, light green color (upper surface), green color (lower surface), no hairs in both surfaces, wedge-shaped - kidney-shaped, medium texture |
| cluster | medium weight, conical with two wings, medium dense, berry skin with green color, firm flesh, neutral taste, no flesh coloration | very low weight, cylindrical-conical, with 1-2 wings, dense, berry skin with green-yellow color, slightly firm flesh, aromatic taste, no flesh coloration | low weight, conical, with 1-2 wings, medium dense, berry skin with green-yellow color, slightly firm flesh, neutral taste, no flesh coloration |
| primocane and floricane | elliptic cross section, brownish color, lenticels: absent, short-medium internodes, diameter: small (about 8 mm) | circular cross section, brownish color, lenticels: absent, short-medium internodes, diameter small (about 8 mm) | oblate cross section, brownish color, lenticels: absent, medium internodes, diameter small (about 8 mm) |
| harvesting time | early (late August in Middle Friuli, North-Eastern Italy), | medium (early September in Middle Friuli, North-Eastern Italy) | Early (late August, Middle Friuli, North-Eastern Italy) |
| resistances | resistant to winter temperature (−22° C.), resistant to downy mildew, tolerant to powdery mildew, when overripe susceptible to cluster rots. | Average resistance to winter temperature (−15° C.), susceptible to downy mildew, susceptible to powdery mildew | resistant to winter temperature not known, resistant to downy mildew, resistant to powdery mildew |

Of the many commercial cultivars known to the present inventor, the most similar to the new grapevine 'SAUVIGNON KRETOS' is the female parent 'Sauvignon', to which a comparison has been provided above.

BRIEF DESCRIPTION OF THE PHOTOGRAPHS

The accompanying photographs illustrate the overall appearance of the new grapevine 'SAUVIGNON KRETOS' showing the colors as true as is reasonably possible with colored reproductions of this type. Colors in the photographs may differ slightly from the color values cited in the detailed botanical description, which accurately describe the color of 'SAUVIGNON KRETOS'.

DETAILED BOTANICAL DESCRIPTION

Figure 1A:
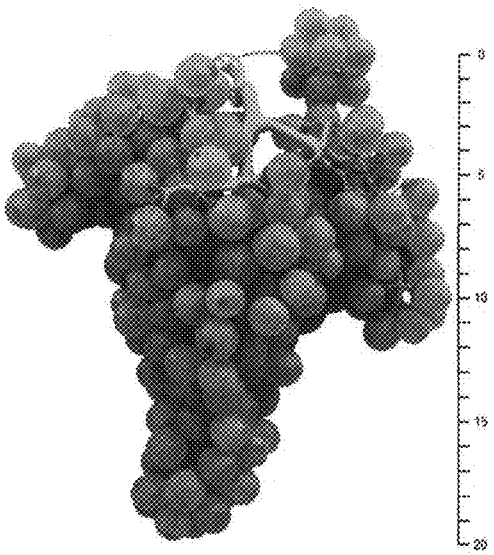
FIG. 1A and FIG. 1B show typical fruit clusters of 'SAUVIGNON KRETOS', taken on Aug. 30, 2012 in Udine, Italy.
Figure 1B:
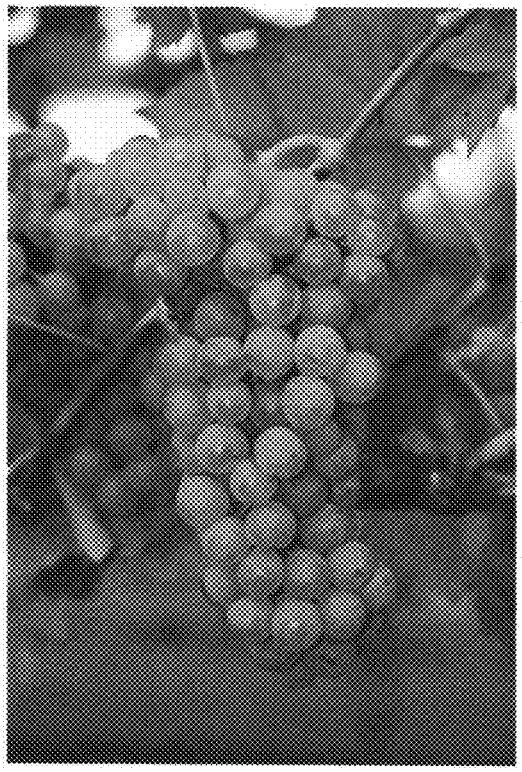
Figure 2:
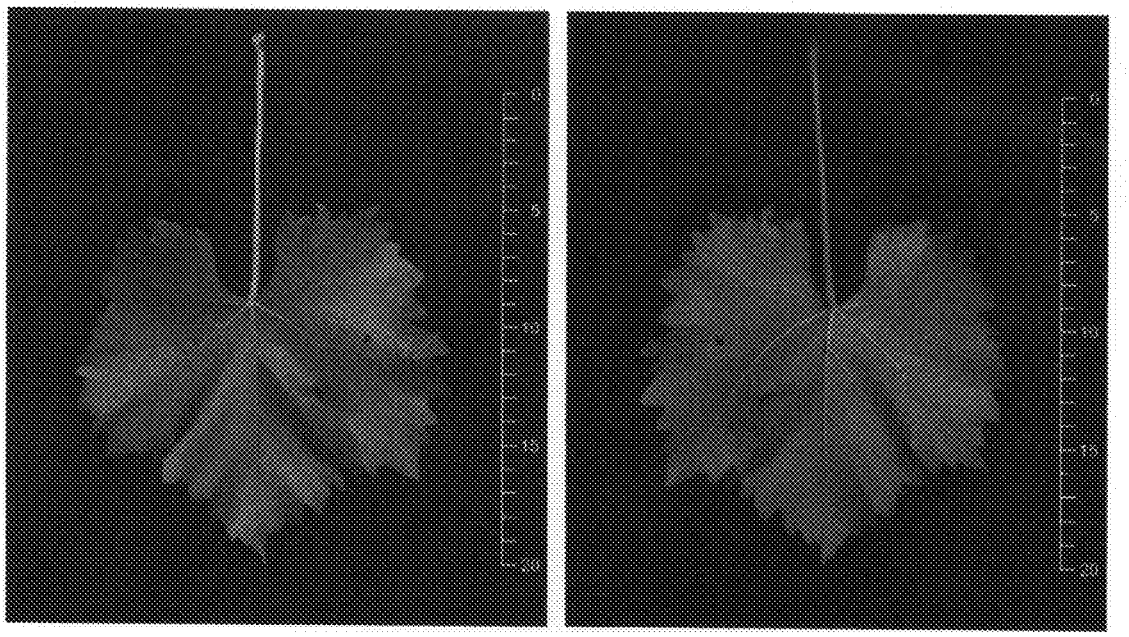
FIG. 2 shows a typical mature leaf (upper surface, left and lower surface, right) of 'SAUVIGNON KRETOS', taken on Jun. 1, 2012 in Udine, Italy.
Figure 3:
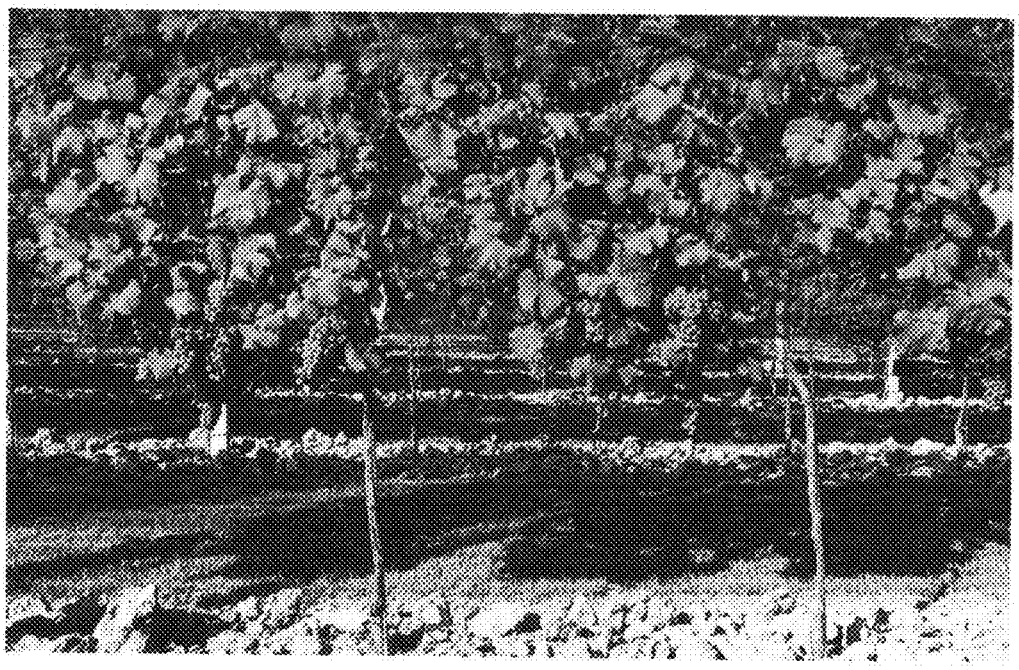
FIG. 3 shows a typical mature vine of 'SAUVIGNON KRETOS', taken on Aug. 3, 2012.
Figure 4:
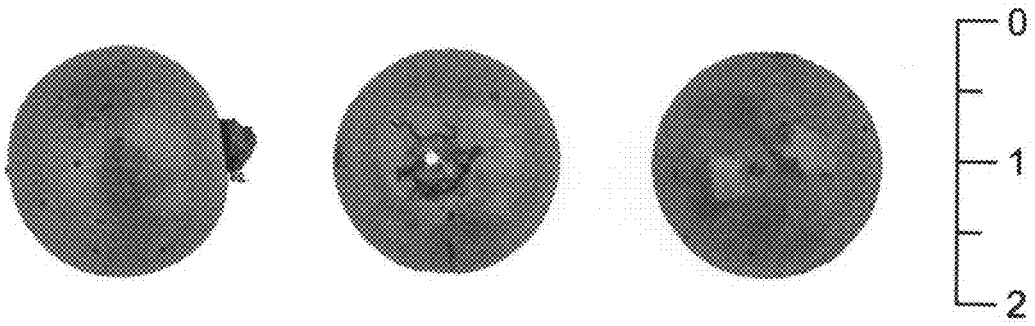
FIG. 4 shows a close-up view of typical mature fruit of 'SAUVIGNON KRETOS', taken on Aug. 30, 2012 in Udine, Italy

The following description of 'SAUVIGNON KRETOS' unless otherwise noted, is based on observations taken during the 2011, 2012, and 2013 growing seasons in Udine, Italy and Fossalon di Grado (GO), Italy, from plants dug from a nursery located in Vivai Cooperativi Rauscedo, Rauscedo (PN), Italy during the beginning of December 2007 and planted approximately 16 to 20 weeks later in Udine, Italy and Fossalon di Grado (GO), Italy. The phenotypical descriptions and color designations stated for the new variety may vary, depending upon variations in environmental factors, including weather (temperature, humidity and light intensity), day length, soil type, location and cultural conditions. 'SAUVIGNON KRETOS' has not been observed under all possible environmental conditions.

Color references are made to The Royal Horticultural Society Colour Chart (R.H.S.), (Edition V, 2007), except where general colors of ordinary significance are used.

TABLE 3

Detailed Botanical Description

| Characteristic | 'SAUVIGNON KRETOS' | Sauvignon (unpatented) |
|---|---|---|
| GENERAL | | |
| Resistance to pest/disease | Resistant to downy mildew, tolerant to powdery mildew | Susceptible to downy mildew and to powdery mildew |
| Resistance to natural elements | Resistant to winter cold down to −22° C. | Resistant to winter cold down to −15° C. |
| VINE | | |
| vigor | strong | medium |
| Trunk diameter | 6.5 | 6.5 |
| Bark | | |
| color | RHS 177B | Dark brown |
| underbark color | RHS 179B | Light brown |
| texture | n.a. | n.a. |
| Canes | | |
| length | Internode length cm 9 | Internode length about cm 11 |
| Width (diameter) | 8 mm | 8 mm |
| Shoots | | |
| shape | Erected, cross section: oblate, | Semi-erected, cross section: circular, |

TABLE 3-continued

| Detailed Botanical Description | | |
|---|---|---|
| Characteristic | 'SAUVIGNON KRETOS' | Sauvignon (unpatented) |
| color | surface: with stripes, nodes and inter-nodes without hairs internodes with red (RHS 185B) and green (RHS 144B) pigmentation on both sides, nodes with red (RHS green (RHS 185B) and 144B) ventral side | surface: smooth, nodes and inter-nodes without hairs Internodes with green color on ventral and dorsal side, nodes with green ventral and dorsal side (RHS 144B) dorsal side and green |
| Tendrils | | |
| form | Bifid or trifid | bifid |
| color | RHS 143B | Green |
| texture | normal | normal |
| number | 2 or <2 consecutive | 2 or <2 consecutive |
| Buds | | |
| size | average | average |
| shape | round | round |
| color | RHS 139C and RHS 181A | Light brown |
| number | 2/node | 2/node |
| time of budbreak | early | early-medium |
| LEAVES | | |
| Size | small-medium | medium |
| Number of leaflets | 5 | 5 |
| Glossiness | Medium-high | medium |
| Cross section shape | V-shaped | V-shaped |
| Color (immature) | | |
| Upper surface | RHS 140B and RHS 185B | Pale green |
| Under surface | RHS 140B and RHS 185B | Pale green |
| Color (mature) | | |
| Upper surface | RHS 141A | Medium green |
| Under surface | RHS 141B | Darker green |
| Petiole | | |
| Length (cm) | 6.2 | 6.0 |
| Color (upper surface) | RHS 145C | green |
| Color (under surface) | RHS 145C | green |
| Stipule orientation | n.a. | n.a. |
| FLOWERS | | |
| Flowering period (time of beginning of flowering) | End of May | End of May |
| Sex | hermaphrodite | hermaphrodite |
| Size | Average | average |
| Diameter(cm) | 0.3 (stamens) | 0.3 (stamens) |
| Stamen Color | RHS 4D | |
| Pistil Color | RHS 149A | |
| Fragrance | average | average |
| Flower number (at 3rd node from tip of lateral mean and range) | n.a. | n.a. |

TABLE 3-continued

| Detailed Botanical Description | | |
|---|---|---|
| Characteristic | 'SAUVIGNON KRETOS' | Sauvignon (unpatented) |
| Petals | | |
| Length (cm) | n.a. | n.a. |
| Width (cm) | n.a. | n.a. |
| Overall shape | calyptra | calyptra |
| Calyptra Color | RHS 134A | green |
| Sepals | None | None |
| Length (cm) | n.a. | n.a. |
| Width (cm) | n.a. | n.a. |
| Overall shape | n.a. | n.a. |
| Color (immature) | n.a. | n.a. |
| Upper surface | | |
| Under surface | | |
| Color (mature) | n.a. | n.a. |
| Upper surface | | |
| Under surface | | |
| Pedicel | | |
| Length (mm) | 7 | 7 |
| Color | RHS 145C | green |
| FRUIT | | |
| Primocane time of fruiting (1st pick) | August 25th | September 7th |
| Clusters | | |
| cluster weight | Low (g 170) | Low (g 230) |
| cluster shape | conical | conical |
| cluster length | mm 180 | medium |
| avg. berries per cluster | 200 | 220 |
| avg. clusters per shoot | 2 | 2 |
| Berries | | |
| Berry size | g 1.8 | g 1.0 |
| Berry length (cm) | 1.76 | 1.50 |
| Berry width (cm) | 1.56 | 1.50 |
| Overall shape of berry | broad ellipsoid | globose |
| Berry Texture | soft | soft |
| Berry Skin Color (immature) | RHS 137C | green |
| Berry Skin Color (mature, at 19° Bx) | RHS 150B | green |
| Berry Flesh Color | RHS 148B | |
| Soluble solids (%) | 22.6 | 21.1 |
| Titratable acidity ( as g/L tartaric acid) | 4.6 | 5.7 |
| Sugar/acid ratio | 4.9 | 3.7 |
| Firmness | soft | soft |
| Seeds | 2-3 | 2-3 |
| Seed Color | RHS 172A and RHS163B | |
| Skin cracking? | no | rarely |
| Juice color | transparent | transparent |
| Berry taste | neutral | neutral |
| Eating quality | n.a. | n.a. |
| Berry uses | wine | wine |
| Shipping quality | n.a. | n.a. |

What is claimed is:

1. A new and distinct grapevine, referred to as 'SAUVIGNON KRETOS', as herein described and illustrated by the characteristics set forth above.

* * * * *